United States Patent
Fuller et al.

(12)

(10) Patent No.: US 6,180,587 B1
(45) Date of Patent: Jan. 30, 2001

(54) MULTIPLE PHASE COMPOSITIONS

(75) Inventors: Robert Langley Fuller, Asbury; Amit Sachdev, Scotch Plains, both of NJ (US); Paul Balot, Wartet (BE)

(73) Assignee: Colgate Palmolive Company, New York, NY (US)

(*) Notice: Under 35 U.S.C. 154(b), the term of this patent shall be extended for 0 days.

(21) Appl. No.: 09/407,393

(22) Filed: Sep. 28, 1999

(51) Int. Cl.$^7$ ............... C11D 3/37; C11D 17/08; A61K 7/48
(52) U.S. Cl. ............... 510/417; 510/434
(58) Field of Search ............... 510/417, 434, 510/405, 426; 166/270, 270.1, 400; 516/53, 54; 424/400, 401, 59, 60

(56) References Cited

U.S. PATENT DOCUMENTS 3,718,609 * 2/1973 Weimer .
4,125,156 * 11/1978 Glinsman .
4,337,159 * 6/1982 Reed et al. .
4,439,345 * 3/1984 Duke .
4,635,722 * 1/1987 Carlin .

FOREIGN PATENT DOCUMENTS 62-263297  11/1987 (JP) .

* cited by examiner

Primary Examiner—Yogendra Gupta
Assistant Examiner—Gregory E Webb

(57) ABSTRACT

A composition comprising a lower aqueous phase having from at least about 1 wt % of the composition of a polymer or copolymer selected from the group consisting of polyacrylate, polystyrene sulfonate, polyvinyl-pyrrolidone, or maleic anhydride and mixtures thereof and an upper aqueous phase having a cleansing effective amount of a surfactant or mixture thereof.

12 Claims, No Drawings

MULTIPLE PHASE COMPOSITIONS

BACKGROUND OF THE INVENTION

Cleansing compositions are generally a single phase or an oily phase dispersed in a watery cleansing phase. When significant quantities of an oily phase are present, particularly to apply skin conditioning via emolliency with lipophilic type components, substantial efforts are usually made to provide a stable emulsion, which does not come apart. However, there can be significant advantages to having two or more phases present in a single container during non-use. These phases can be appealing to the eye depending upon various agents; particularly coloring agents dispersed therein or particles present at the interface of the phases. A small amount of shaking by the user prior to end use can create mixing of the phases and at times a bubbly-type appearance. Emulsion(s) can be formed during the mixing and can be present during the actual cleansing. Upon nonagitation, the phases once more readily separate into two or more phases and are ready for the next cleansing, for example, twenty-four hours later when using a shower gel. Though, lower viscosities are acceptable for products such as bath foam, higher viscosities are preferred for certain products such as shower gels, cream-like compositions, and the like.

However, making two aqueous phases is not readily achievable. Secondly, the selective thickening of one aqueous phase, as opposed to the second, is also not readily achievable.

SUMMARY OF THE INVENTION

In accordance with the invention, there is a composition comprising a lower aqueous phase having therein from at least about 1% desirably at least about 2 wt. % of the composition of a hydrophilic polymer or copolymer selected from the group consisting of polyacrylate, polystyrene sulfonate, polyvinylpryrrolidone, or maleic anhydride and mixtures thereof and an upper aqueous phase having therein a cleansing effective amount of a surfactant or mixture thereof.

When the lower polymer phase is formed, it is desirable that at least about 10% of the volume of the composition be in the lower phase.

It is preferred that the viscosity of the composition when mixed should be at least 200 centipoise and no more than about 15,000 centipoise.

Though selective choice of polymers a third phase can be formed. This phase is a second aqueous polymer phase below the first aqueous polymer phase. This results in a three phase composition having a surfactant phase which lies above a first polymer place and the first polymer phase lies above a second polymer phase.

DETAILED DESCRIPTION OF THE INVENTION

The two aqueous phases form distinct separate layers when in contact without agitation. Normally when a water-soluble polymer is present with a water soluble or dispersible surfactant (such as a nonionic ethoxylated surfactant) a single aqueous layer is formed. It has now been found that certain skin compatible polymers will not normally coexist in a single aqueous layer with a surfactant but will form a second layer, usually below that of the surfactant containing aqueous layer. It is believed that the property which separates this grouping of polymers from the ones that are compatible in one phase, is the hydrophilicity of the polymer. Those polymers which are highly hydrophilic will form a second aqueous phase. These polymers typically have no or very little cross-linking and no significant hydrophobic bonding. Examples of polymers, which form such a second aqueous phase are polyacrylate polymers (including copolymers) polystyrene sulfonate(s), polyvinylpyrrolidones and the like. Examples of polymers, which do not form a second phase but maintain a single phase with the aqueous surfactant-containing phase, are polyethylene glycols, Pluronics (ethylene oxide polymers and copolymers with propylene oxide, cellulosic polymers, and the like.

The greater the quantity of hydrophilic polymer employed in the composition, the larger the volume of the polymer containing phase. Generally the higher the molecular weight the greater the propensity for the polymer to be present in the phase separate from the surfactant phase. The lower the molecular weight the more the polymer partitions with the surfactant phase until there may be only one phase at relatively low polymer molecular weights. When using polyvinylpyrrolidone polymer greater than about 60,000 molecular weight and with other polymers present, a second polymer phase can be formed which is below the first polymer phase. This results in a three phase system with surfactant layer on top, a first polymer phase having the high molecular weight polyvinylpyrrolidone and the second polymer phase below the first polymer phase having the other polymers mentioned before such as the polyacrylate maleic anhydride. It should be noted that there is always some partitioning of the surfactant and polymer(s) in all the phases. However, when referring to a "surfactant phase", the phase is rich in surfactant compared to the other phase(s). The same applies to "first polymer phase" and "second polymer phase".

In the same manner as various polymers having a tendency to associate with the surfactant in a single aqueous phase, so do the usual thickening components. This phenomenon therefore provides a reasonably viscous surfactant phase and a very thin polymer-containing phase prior to thickening. Examples of thickening agents which preferentially enter the aqueous surfactant phase as opposed to the polymer phase are common salt such as sodium chloride, associated thickeners such as polyacrylate methacrylates with cross linking such as Aculyn 22 and 33, see CTFA vol. 4, 1991 for further definition, and hydrophobically modified polymers.

With respect to the two phase system, this preferential solubility leaves a two aqueous phase composition which is heavily imbalanced with respect to viscosity, the upper surfactant phase being substantially more viscous than the lower polymer phase. It is difficult to achieve proper mixing when the two-phase composition is agitated. However, some thickeners are preferentially soluble in the polymer phase. These materials include the non-hydrophobically modified water-soluble polymers, which may or may not be crosslinked. Examples of such polymers include polyacrylic acids and polyacrylic acids crosslinked with an allyl ether of pentaerythritol and the like, of sucrose or of propylene, for example, the Carbomer 900 series available from Goodrich as "Carbopol(s)". Such polyacrylic acids are 70 to 100% neutralized with a base.

Additionally, it has been observed that certain metallic salts also bring about preferential thickening of the polymer phase as opposed to the surfactant phase. These salts are the water soluble metallic salts having a cation with an oxidation number of at least plus two. Examples of such salts include magnesium, calcium, barium, manganese, iron, aluminum and the like. Various anions include chloride, nitrate, sulfates and the like of these metallic salts. Magnesium chloride is preferred.

Once the polymer containing aqueous phase is thickened to the desired viscosity, standard agents such as common salt (sodium chloride), associative thickeners such as Aculyn 22 and 33, and hydrophobically modified polymers can thicken the surfactant containing aqueous phase.

The surfactant containing aqueous phase has any surfactant or mixtures thereof which can be employed in a cleansing composition. There is a skin cleansing effective amount of a surfactant present in the composition. Soap, a long chain alkyl or alkenyl, branched or normal carboxylic acid salt such as sodium, potassium, ammonium or substituted ammonium salt can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition.

Other surfactants can be present in the composition as well. Examples of such surfactants are the anionic, amphoteric, nonionic and cationic surfactants. Examples of anionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

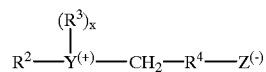

wherein $R^2$ contains an alkyl, alkenyl, or hydroxy alkyl radical of from about 8 to about 18 carbon atoms, from 0 to about 10 ethylene oxide moieties and from 0 to I glyceryl moiety; Y is selected from the group consisting of nitrogen, phosphorus, and sulfur atoms; R3 is an alkyl or monohydroxyalkyl group containing 1 to about 3 carbon atoms; X is I when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, etc. The sulfo-betaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;

laurylpyridinium chloride;

cetylpyridinium chloride laurylpyridinium chloride;

laurylisoquinolium bromide;

ditallow(Hydrogenated)dimethyl ammonium chloride;

dilauryldimethyl ammonium chloride; and stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

$$R_1R_2R_3N \rightarrow 0$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl)amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexa-decylamine oxide.

5. Long chain tertiary phosphine oxides corresponding to the following general formula:

$$RR'R''P \rightarrow 0$$

wherein R contains an alkyl, alkenyl or monohydroxyalkyl radical ranging from 8 to 20 carbon atoms in chain length, from 0 to about 10 ethylene oxide moieties and from containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethyl-phosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

The quantity of polymer which can be utilized in the composition to form the polymeric layer(s) is an amount sufficient to form an aqueous layer separate from the aqueous surfactant-containing layer. Generally, this should be a minimum of at least about 1.0 wt. % of the composition, desirably it least about 2.0 wt %, 3.0 wt. % or 4.0 wt. % of the composition. The maximum amount is generally dependent upon economics but is usually no more than about 20 or even about 15 wt. % of the composition. A preferred polymer is a polyacrylic having a maleic anhydride comonomer, Sokalan® CP5 available from BASF. It has a molecular weight of 70,000. As stated previously, generally the higher the molecular weight of the polymer, the more favorable the formation of the polymer phase(s) and the greater the partition coefficient between the polymer phase and the surfactant phase for the polymer. When using Sokalan CP5, the molecular weight of the polymer is generally above about 65,000 or even more desirably above about 75,000.

The quantity of thickeners, which can be employed to thicken the polymer phase of the two phase surfactant, polymer system, is naturally dependent upon the desired viscosity of the polymer phase. Generally, at least about 0.1, 0.2 or 0.3 wt. % of the thickeners as based upon the composition can be employed. The maximum amount is generally dependent upon economics and the highest viscosity which is compatible with the surfactant phase and a compatible gel or flowing like system after mixing. The maximum generally does not exceed about 5, 4 or 3 wt. % of the composition. The most desirable thickener is Carbopol 910 from Goodrich, which demonstrates a good mix of properties, for example degree of cross-linking, molecular weight, and smoothness of flow.

The quantity of metallic salts which can be employed as thickening agent for the polymer phase is at least about 0.5 or 0.75 wt % of the composition. Generally, levels above about 3 or 2.5 wt % of the composition should not be exceeded.

When three phases are present, surfactant phase, first polymer phase (heavy polyvinylpyrrolidone [PVP]), and second polymer phase (other polymers), the first polymer phase is thickened by utilizing higher molecular weight PVP.

The quantity of surfactant is a cleansing effective amount of surfactant or mixture thereof. Generally, the surfactant should be at least about 5 wt. % of the composition, or desirably at least about 7, 8 or 9 wt. %. The maximum amount is that quantity which remains compatible with the overall properties of the composition. Generally, no more than about 30, 25 or 20 wt. % is exceeded. For overall foaming, it is desirable to use at least some anionic surfactant. This is usually at least about 20 wt. % of the surfactant mixture. Cationic surfactant(s) can be omitted if desired.

Since these thickeners and polymers all form equilibrium systems, the order of addition is not significant. However, carbomers generally require a large amount of water to disperse. Thickeners, which can be employed in the surfactant layer, are the usual ones including salt such as sodium chloride, glucamate dioleate ester, pentaerythritol oleate, Aculyn 22, 33, and the like.

The viscosities of the surfactant layer and the polymer layer are desirably as close together as possible so that a good emulsion or dispersion will occur when agitation is done. However, generally the polymer layer is of lower viscosity than the surfactant layer because of formulation issues and/or economics. The viscosity of the polymer layer is about 100 to about 4,000 centipoise desirably no more than about 3,000 cps. The viscosity of the surfactant layer is generally from about 100 to about 15,000 centipoise, generally no more than about 10,000; or 5,000 cps. The polymer layer viscosity is desirably about 100% of the surfactant layer viscosity but can be as low as about 15–20% of the surfactant layer viscosity for the two layer surfactant, polymer system. All centipoise are measured on a Brookfield RVT viscometer at 23° C. using a 5 spindle at 20 rpm.

There can also be present in the composition essentially water insoluble oily material for general emolliency purposes. Materials, which can be used, include the following:
1. Hydrocarbon oils and waxes, Examples thereof are mineral oil, petrolatum, paraffin, ceresin, ozokerite, microcrystalline wax.
2. Silicone oils, such as dimethyl polysiloxanes, methylphenyl polysiloxanes, silicone glycol and copolymers.
3. triglyceride esters, for example vegetable and animal fats and oils.
4. glyceride esters and esters such as acetylated monoglycerides and ethoxylated onoglycerides.
5. Alkyl and alkenyl esters of fatty acids having 10 to 20 carbon atoms. Examples include hexyl laurate, isohexyl laurate, isohexyl palmitate, isopropyl myristate, isopropyl palmitate, decyl oleate, isodecyl oleate, hexdecyl stearate, decyl stearate, isopropyl isostearate, diisopropyl adipate, diisohexyl adipate, dihexyldecyl adipate, diisopropyl sebacate, lauryl lactate, myristyl lactate, lactyl lactate, oleyl myristate, oleyl stearate and oleyl oleate.
6. Fatty alcohols having 10 to 20 carbon atoms, lauryl, myristyl, cetyl, hexadecyl, stearyl, isostearyl, hydroxystearyl, oleyl, ricinoleyl, behenyl, erucyl, and 2-octyl dodecanyl alcohols and examples of satisfactory fatty alcohols.
7. Lanolin and derivatives, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols and lanolin alcohols linoleate are illustrative emollients derived from lanolin.
8. Natural waxes, esters thereof and ethoxylated natural waxes, beeswax, spermaceti, myristyl myristate, stearyl stearate, polyoxyethylene sorbitol beeswax, cannauba wax and candelilla wax.

Quantities of the emollient which can be employed are any skin conditioning effective amount of material. Generally a minimum of about 0.1 or 0.2 wt. % of the composition is desirable. The upper limit is not unduly significant but is below the amount wherein the composition is no longer compatible upon standing or agitation. Therefore, an amount below about 40 wt. %, 35 or 30 wt % is useful. Upon addition of the oily substance to the composition, an additional phase, usually above the surfactant phase, may be present in the composition. Formation of this additional phase, depends upon the solubility and quantity of the emollient present. For example, PEG-7 glyceryl cocoate is readily dispersible in the water at relatively low quantities, about 1%. However, large quantities of mineral oil, about 30 wt % of the composition, forms an additional phase above the surfactant phase.

Other functional materials can also represent in the composition, for example, antimicrobial agents, preservatives, UV stabilizers, colorants, solid materials for exfoliative purposes or physical appearance and the like. Of these, the more interesting are materials which will significantly partition between the phases or gather together at the interface of the two major layers. With respect to the colorants, the following coloring agents can be found in significant quantities in the polymer phase: Yellow #5, #6, #10; Red #4; Blue #1. The following colorants are significantly soluble in the surfactant phase: Violet #2, Orange #4 and Green #5 (all FD&C or D&C notation).

Enough colorant should be employed to provide color and intensity desired. These are well known in the art.

With respect to the solid particles insoluble in the phases virtually any particle can be used for its color, shape or desired exfoliative or other function. However, the density of the particle should be such that it is present primarily, desirably almost exclusively at the interface of the layers or even more desirably suspended relatively uniformly throughout at least one of the layers. Generally, the alginates density are such that they are desirably employed in the composition and gather primarily at the interface of the surfactant layer and polymer layer. Other materials, which can be employed, are polyethylene or polypropylene beads. The quantities are as generally known in the art for the specification function but are generally at least about 0.3, 0.5 or 1.0 wt. % of the composition and are generally not above about 2, 5 or 10 wt. % of the composition. The densities of these materials are desirably from about 1.00 to about 1.08 g/cc or 1.03 to about 1.06.

The pH of the composition is not unduly significant and can range from about 4 to about 8 while maintaining compatibility of the composition with skin.

The following are examples of the invention. These examples are intended to illustrate the scope of the invention and are not intended to unduly limit the nature and breadth of the invention.

The compositions of the invention are prepared by standard means, essentially preparing the surfactant phase by mixing together the components thereof at room temperature or elevated temperature if necessary followed by mixing the components of the polymer phase at room temperature or elevated temperature if desired and then mixing together both of these portions of the composition. Alternatively, all materials can be added sequentially to the same vessel.

EXAMPLE 1

| Component | Wt % |
| --- | --- |
| Carbomer 910 (MW = 750K) | 0.80 |
| Hexylene Glycol | 2.5 |
| SLES - Laureth 2-Ethyoxy Sulfate | 9.00 |
| Cocoamidopropyl Betaine | 3.00 |
| PEG-7 Glyceryl Cocoate | 0.20 |
| Tetrasodium EDTA | 0.05 |
| DMDM Hydantoin | 0.22 |
| Acrylic/Maleic Copolymer (MW = 70K) | 6.00 |
| Sodium Hydroxide Solution (50%) | 0.20 |
| Sodium Chloride | 0.80 |
| Deionized Water | QS |

Two phases form when mixed upon standing. The viscosity of the upper surfactant phase is 2,500 cps. The viscosity of the lower polymer phase is 1,100 cps. The viscosity of the composition when mixed is 2,000 cps.

EXAMPLE 2

| Component | Wt % |
| --- | --- |
| SLES - Laureth 2-Ethyoxy Sulfate | 9.00 |
| Hexylene Glycol | 2.80 |
| Cocoamidopropyl Betaine | 7.50 |
| PEG-7 Glyceryl Cocoate | 0.20 |
| DMDM Hydantoin | 0.22 |
| Acrylic/Maleic Copolymer (MW = 70K) | 12.00 |
| Magnesium Chloride Hexahydrate | 1.50 |
| Deionized Water | QS |

Two phases form when mixed.

Upon standing, the viscosity of the upper surfactant phase is 1,800 cps and the viscosity of the lower polymer phase is 300 cps.

EXAMPLE 3

| Component | Wt. % |
| --- | --- |
| SLES - Laureth 2-Ethyoxy Sulfate | 9.00 |
| Hexylene Glycol | 2.50 |
| Cocoamidopropyl Hydroxylsultaine | 3.00 |
| PEG-7 Glyceryl Cocoate | 0.20 |
| Tetrasodium EDTA | 0.05 |
| DMDM Hydantion | 0.22 |
| Acrylic/Maleic Copolymer (MW = 70K) | 6.00 |
| Polyvinyl Pyrolidone (MW = 350K) | 2.00 |
| Citric Acid Solution (50%) | 0.20 |
| Deionized Water | QS |

The Batch splits into 3 phases after 2 days standing.

| | Bottom | Middle | Top |
| --- | --- | --- | --- |
| Volume | 40% | 11% | 49% |
| Viscosity - No thickeners | <20 cps | 120 cps | 100 cps |

What is claimed is:

1. A composition comprising a lower aqueous phase having from at least about 1 wt % of the composition of a hydrophilic polymer or copolymer having a unit derived from a monomer selected from the group consisting of acrylic, styrene sulfonate, vinyl pyrrolidone, and maleic anhydride; and mixtures of said polymers and copolymers and an upper aqueous phase having a cleaning effective amount of a surfactant or mixture thereof.

2. The composition in accordance with claim 1 wherein the lower aqueous phase has at least about 10% of the volume of the composition.

3. A composition wherein upon agitation the separate aqueous phases of claim 1 mix and a viscosity of the overall composition of about 100 to about 15,000 centipoise is obtained.

4. The composition in accordance with claim 1 wherein the lower aqueous phase is thickened with a thickener selected from the group consisting of non-hydrophobically modified polymer, water soluble metallic salt having a cation with an oxidation number of at least plus two, or mixtures thereof.

5. The composition in accordance with claim 4 wherein the thickener is a polyacrylic acid or cross-linked polyacrylic acid.

6. The composition in accordance with claim 4 wherein the salt is magnesium chloride.

7. The composition in accordance with claim 1 wherein the polymer in the lower aqueous phase is a polyacrylic maleic anhydride copolymer.

8. The composition in accordance with claim 4 wherein the polymer in the lower aqueous phase is a polyacrylic maleic anhydride copolymer.

9. The composition in accordance with claim 1 wherein the viscosity of the lower layer is about 100 to about 4,000 centipoise.

10. The composition in accordance with claim 1 wherein the viscosity of the upper phase is from about 100 to about 15,000.

11. The composition in accordance with claim 1 wherein the viscosity of the lower layer is at least about 20% of the viscosity of the upper layer.

12. A composition having three aqueous phases comprising:

(a) a top aqueous phase having a cleaning effective amount of a surfactant or mixture thereof;

(b) a lower aqueous phase having at least about 1 wt % of the composition of a high molecular weight polyvinylpyrrolidone polymer or copolymer, and (c) a lowest aqueous phase having at least about 1 wt % of the composition of a hydrophilic polymer or copolymer having a unit derived from a monomer selected from the group consisting of acrylic, styrene sulfonate, vinyl pyrrolidone, and maleic anhydride; and mixtures of said polymers and copolymers.

* * * * *